United States Patent [19]

Lynch et al.

[11] Patent Number: 4,529,605
[45] Date of Patent: Jul. 16, 1985

[54] BATHING OIL COMPOSITION

[75] Inventors: Una E. Lynch, 27 McBride, White Plains, N.Y. 10603; Bonnie J. Daniel, St. Paul, Minn.

[73] Assignee: Una E. Lynch, White Plains, N.Y.

[21] Appl. No.: 457,432

[22] Filed: Jan. 12, 1983

[51] Int. Cl.³ ............................................. A61K 47/00
[52] U.S. Cl. .................................. 514/552; 514/785; 514/788; 514/182; 514/873
[58] Field of Search .......................................... 424/365

[56] References Cited

U.S. PATENT DOCUMENTS

| | | | |
|---|---|---|---|
| 3,624,208 | 11/1971 | Schmolka | 424/365 |
| 3,976,789 | 8/1976 | Tomita et al. | 424/365 |
| 4,017,641 | 4/1977 | Di Guilio | 424/365 |
| 4,036,991 | 7/1977 | Stiefel | 424/365 |

FOREIGN PATENT DOCUMENTS

| | | | |
|---|---|---|---|
| 0008105 | 2/1980 | European Pat. Off. | 424/365 |
| 2612038 | 10/1976 | Fed. Rep. of Germany | 424/365 |
| 1321406 | 2/1963 | France | 424/365 |
| 47-46331 | 11/1972 | Japan | 424/365 |
| 49-28982 | 7/1974 | Japan | 424/365 |
| 111227 | 9/1975 | Japan | 424/365 |
| 48209 | 9/1982 | Japan | 424/365 |
| 1077016 | 7/1967 | United Kingdom | 424/365 |

OTHER PUBLICATIONS

Stolar, 9/1966, vol. 17, No. 10, pp. 607-621, Journal Society Cosmetic Chemists.
Chem. Abs., vol. 86, 60420x (1977).
Chem. Abs., vol. 80, 40951u (1974).
Chem. Abs., vol. 85, 130380q (1976).
Chem. Abs., vol. 93, 31633h (1980).
Chem. Abs., vol. 83, 209331s (1975).
Chem. Abs., vol. 97, 222754r (1982).
Knox, J. M. and Everett, M. A., "The Oil Bath," *A.M.A. Archives of Dermatology*, vol. 78, p. 642, Jul.--Dec. 1958.
Wells, F. V. and Lubowe, I. I., *Cosmetics and the Skin*, pp. 332-333, Reinhold Publishing Corporation, New York, 1964.
Goldemberg, R. L., "Bath Oils," *Cosmetics & Toiletries*, vol. 94, pp. 55, 58, Jul. 1979.

*Primary Examiner*—Dale R. Ore
*Attorney, Agent, or Firm*—Kinney & Lange

[57] ABSTRACT

A soluble bathing oil composition is prepared from a cationic surfactant, a nonionic surfactant, and an emollient. The composition produces a fine emulsion in bath water for both cleansing the skin and depositing an emollient layer on the skin.

7 Claims, No Drawings

BATHING OIL COMPOSITION

BACKGROUND OF THE INVENTION

1. Field of the Invention

The present invention relates to bathing oils, and in particular, it relates to bathing oils which are readily dispersed within bath water.

2. Description of the Prior Art

In order to understand the requirements for an improved bathing oil, it is necessary to have some knowledge of the characteristics of the skin, especially its anatomy and physiology. Human skin is made up of layers and the outermost layer is itself composed of five different strata. The innermost stratum of the surface layer is the source of the cells for the others. Cells are constantly produced here by mitosis. One daughter cell remains in the stratum and the other pushes upward toward the surface, flattening and ultimately dying in a process called keratinization. These keratinized epithelial cells move through the outermost or keratin layer to the surface, where they are constantly shed and replaced.

Normal skin is almost waterproof because of the presence of a nongreasy, almost undetectable emollient film. Except for the palms of the hands and soles of the feet, skin contains sebaceous glands which secrete sebum, a complex mixture of fats, waxes and sterols which flows over the keratin layer, coating it with a thin, hydrophobic or waterproof film. After menopause, the secretion of sebum decreases so that dry skin is a very common problem for older women. Dry skin can also occur in younger individuals with normal skin as the result of exposure to wind or low humidity. In addition, the use of detergents, especially anionics, for skin cleansing can cause dry skin because they are such effective oil emulsifiers that they strip the skin of its natural oil.

Although dry skin, which is scaly and itchy, lacks water, soaking it in water, paradoxically, makes the condition worse. Because such skin is deficient in sebum, it absorbs water when immersed in water, swells, and becomes even more permeable to water. Upon removal from the water, water rapidly passes through the swollen skin leaving it drier than before.

Because of the natural, constant shedding and replacement of cells at the surface of the skin, there is no need to scrub the skin in order to cleanse it. In fact, it is harmful to do so because this layer is an important component of the protective barrier of the body. If this layer is removed by scrubbing or by accident, the whole process of skin growth is accelerated, but the time required for replacement is at least one day.

Although oils have been used in bathing since antiquity, they were not widely used in this country until relatively recently. In 1958, a group of dermatologists suggested bathing in an oil bath for the treatment of certain pathological skin conditions such as dry, chronic dermatosis. (Knox, John M., Everett, Mark Allen and Curtis, Arthur C., *Arch. of Dermatology*, 78, 642 (1958)). The bathing oil formulation consisted of a mixture of an alkylarylpolyether alcohol and an oil, either vegetable or mineral, which was to be added to a tubful of water in which the patient soaked for a short time. Knox et. al. reported that the "oil bath is an excellent therapeutic agent which is easily prepared and is effective in the treatment of selected dermatological conditions in which the skin is abnormally dry but not excessively inflamed."

Since then a variety of bathing oils have been produced and sold. The primary function of the early, popular bath oils was to perfume the bath and these products were sold as cosmetics, not drugs. According to Wells and Lubowe (Wells, F. V. and Lubowe, Irwin I., *Cosmetics and the Skin*, Reinhold Publishing Co., N.Y., 1964, p. 333), a "true bath oil is virtually water insoluble and when poured into the bath should form a perfumed oily film that spreads over the surface of the water producing a maximum diffusion of fragrance. Any oil left on the body should feel pleasantly emollient, neither greasy nor sticky and then the inevitable bath tub 'ring' should be easily removable."

These bath oils, now called "floating bath oils" contained large amounts, up to 75% by weight, of perfume. The remaining ingredients are an oil, either vegetable or mineral, a small amount of a fatty alcohol to promote spreading and a small amount of a surfactant to aid in cleaning the tub.

The Schmolka U.S. Pat. No. 3,624,208 issued on Nov. 30, 1971 describes one such "floating bath oil" composition. The Schmolka Patent states that bath oils may be classified as "spreading bath oils; dispersible bath oils; highly perfumed bath oils; soluble bath oils; foaming bath oils; and germacidal bath oils. The first three can be considered true bath oils, while the latter three are aqueous preparations containing solubilized oil." The Schmolka Patent states that a bath oil should be a sparkling clear solution, and that, when poured into a tub of water, should spread rapidly and evenly on the surface of the warm water. The Schmolka Patent describes an improved spreading bath oil which does not form unattractive blobs on the surface of the bath water, which is not greasy on the skin and which does not leave an oily scum on the emptied tub.

However, such bath oils have not been entirely satisfactory. Robert L. Goldenberg points out (Goldenberg, Robert L., *Cosmetics and Toiletries*, 94, #7, 55 (1979)), that floating bath oils have "the disadvantages that the amount of oil deposited is often not uniform as the bather arises from the tub and that a calcium scum produced by the use of soap as a cleansing agent causes problems."

SUMMARY OF THE INVENTION

The present invention includes a bathing oil composition that is readily dispersed within bath water. The bathing oil both cleanses the skin and deposits a moisturizing emollient on the skin. The composition includes a cationic and a nonionic surfactant. The nonionic component is selected from the group of ethylene oxide adducts of ethylene diamine, fatty esters, and fatty alcohols; block polymers of ethylene oxide and diethanolamine derivatives of fatty acids. The cationic component has a relatively high molecular weight greater than approximately 300 and has a positively charged nitrogen. The emollient is selected from the group of synthetic esters of a fatty acid or a mixture of a synthetic ester and a natural oily fat such as sunflower or soy oil.

DETAILED DESCRIPTION OF THE PREFERRED EMBODIMENT

The present invention is a bathing oil composition which is readily dispersed into warm water. The bathing oil is dispersed as a fine emulsion and both cleanses the skin and deposits an emollient layer on the skin to protect the skin.

The bathing oil consists of a nonionic surfactant, a cationic surfactant and a water insoluble emollient. Both surfactants cleanse the skin and the nonionic surfactant also emulsifies the emollient, dispersing it throughout the bath water so that the emollient is readily available for deposition on the skin.

However, it has been found that there is a synergistic interaction between the cationic and the emulsified emollient. Using a nonionic surfactant without a cationic surfactant will not cause proper deposition of the emulsified emollient onto the skin. Using the cationic surfactant without the nonionic surfactant will also not cause the emollient to be deposited on the skin since the emollient would merely float on the surface. However, the bathing oil composition of the present invention containing both a cationic surfactant and a nonionic surfactant causes deposition of an emollient layer on the skin.

A further surprising result of the present invention is the selectivity of the deposition of the emollient layer. The bathing oil composition of the present invention deposits the emollient layer only on the skin of the bather and not on any other surface, such as on the tub. It is believed that the cationic surfactants used in the present invention aid in bonding the emollient to the skin. Although the exact mechanism is unknown, it is believed that a bond is developed between nitrogen atoms contained in the various types of molecules that make up the skin and oxygen atoms contained in the emollient molecules. The selective deposition of the emollient layer does not occur unless the cationic surfactants of the present invention are included in the bathing oil composition.

The cationic surfactant has a relatively high molecular weight greater than approximately 300 and has at least one positively charged nitrogen. The preferred cationic surfactants include dimethyldialkyl ($C_{10}$–$C_{14}$) ammonium chloride, the salts of polyoxyethylene adducts of primary amines containing approximately 12 to 18 carbon atoms, and morpholine based quaternary compounds which are cationic and surface active such as stearamido propyl morpholine lactate and isostearamido propyl morpholine lactate.

The preferred nonionic surfactant includes ethylene oxide, and, preferably, ethylene oxide and propylene oxide block polymers; ethoxylated and propoxylated fatty acids and fatty alcohols; block polymers of ethylene oxide, or ethylene oxide and propylene oxide; and diethanol amine derivatives of fatty acids.

Anionic surfactants are not suitable substitutes for the cationic surfactant since they interfere with the deposition of an emollient layer on the skin in the bath water. In addition, it has been found that anionic surfactants also irritate the skin.

The preferred ratio of the cationic surfactant to the nonionic surfactant is in the approximate range of 0.15 to 1.0. The maximum total surfactant concentration in the bathing oil composition is approximately 50%.

The primary emollient is a hydrophobic organic substance that has at least one oxygen. Preferably, the primary emollient component is a synthetic ester of a fatty acid, or a mixture of a synthetic ester and a natural oil fat, such as sunflower or soy oil. Small amounts of esters of fatty alcohols may also be included in the primary emollient. The purpose of the emollient layer is to coat the skin and prevent drying of the skin which results in scale and itching.

An additional or secondary emollient mixture has been found to improve the present invention. The additional emollient mixture aids in alleviating patches of dry skin while helping further to moisturize the skin. The additional emollient mixture makes the entire emollient more similar to sebum, which is naturally found on the skin. The secondary emollient mixture preferably includes lanolin oil or alcohol, ethoxylated derivatives of lanolin oil, a fatty (aliphatic) alcohol in the range of $C_{12}$–$C_{18}$), a solid fatty (aliphatic) acid in the range of $C_{14}$–$C_{18}$ and lecithin Mineral oil is not a desirable component in the present invention. Mineral oil does not adhere to the skin in the presence of the surfactants of the present invention, as do the preferred emollients.

The preferred concentration of the total emollient fraction is approximately in the range of 58–84% of the composition by weight. The ratio of total emollient fraction to the surfactant fraction in the bathing oil is preferably between 1.7 and 5.4.

Other ingredients may be added to the bathing oil for esthetic and other reasons. For example, a perfume is added for cosmetic reasons. In addition, an alcohol vehicle and a preservative for minimizing oxidation and bacterial growth may also be added.

The preparation of the bathing oil is accomplished by gently mixing the various components described above in a suitable container or vessel. The composition is mixed until a homogeneous product is obtained. Any traces of insoluble solids are filtered off or decanted after settling for approximately 24 hours.

The invention is further illustrated in the following examples which describe various formulations of the bathing oil but are not intended to limit the present invention in any way. The data presented in the examples below are percentages on a weight basis of the total composition. The amount of alkylation of the nonionic and cationic surfactants are average values.

EXAMPLES 1–6

| Components | 1 | 2 | 3 | 4 | 5 | 6 |
|---|---|---|---|---|---|---|
| 1. Primary Emollient | | | | | | |
| isopropyl myristate | 1.1 | 72.1 | 72.2 | 70.7 | 66.5 | 34.3 |
| butyl myristate | 35.6 | | | | | 34.2 |
| isopropyl palmitate | 35.6 | | | | | |
| 2. Secondary Emollients | 1.1 | 1.1 | 1.1 | 1.0 | 0.8 | 1.2 |
| 3. Nonionic Surfactant | | | | | | |
| a | 13.3 | 13.4 | 13.4 | 13.1 | 12.4 | |
| b | | | | | | 12.7 |
| 4. Cationic Surfactant | | | | | | |
| d | 13.3 | 13.4 | 13.4 | 13.1 | 12.4 | 12.7 |
| 5. Perfume | | | | 2.1 | 4.2 | 4.9 |
| 6. Ethanol | | | | | 3.7 | |
| CATIONIC/NONIONIC RATIO | 1.00 | 1.00 | 1.00 | 1.00 | 1.00 | 1.00 |
| TOTAL EMOLLIENT % | 73.2 | 73.2 | 73.1 | 71.7 | 67.4 | 69.7 |
| EMOLL/SURFACTANT RATIO | 2.74 | 2.73 | 2.65 | 2.72 | 2.72 | 2.74 | a = Polyoxypropylene (6) polyoxyethylene (11) fatty ether, where the chain length of the alcohol is approximately between 12 and 18.
b = Polyethoxylated polypropoxylated short chain ($C_{10}$–$C_{12}$) fatty alcohol sold under the tradename Plurafac C-17 by BASF Wyandotte Corporation of Michigan.
d = Polyoxyethylene (15) lauryl/myristylamine.

Examples 1–6 produced a satisfactory bathing oil that cleansed the skin and deposited a layer of emollient on the skin.

EXAMPLES 7-12

| Components | 7 | 8 | 9 | 10 | 11 | 12 |
|---|---|---|---|---|---|---|
| 1. Primary Emollient | | | | | | |
| isopropyl myristate | 34.3 | 64.4 | 48.4 | 60.9 | 0.7 | 66.0 |
| butyl myristate | 34.2 | | | | 35.8 | |
| isopropyl palmitate | | | | | 35.8 | |
| 2. Secondary Emollients | 1.2 | 1.3 | 0.8 | 1.2 | 0.6 | 1.2 |
| 3. Nonionic Surfactant | | | | | | |
| a | 12.7 | | | 13.0 | 13.4 | 7.0 |
| b | | 15.8 | 11.9 | 4.0 | | 2.2 |
| 4. Cationic Surfactant | | | | | | |
| d | 12.7 | 16.3 | 12.2 | 10.0 | 13.4 | 12.7 |
| 5. Perfume | 4.9 | 1.0 | 4.4 | 1.8 | | 1.1 |
| 6. Preservative | | 0.2 | 0.1 | 0.2 | 0.2 | |
| 7. Ethanol | | 1.1 | 22.1 | 9.0 | | 9.8 |
| CATIONIC/NONIONIC RATIO | 1.00 | 1.03 | 1.03 | 0.59 | 1.00 | 1.00 |
| TOTAL EMOLLIENT % | 69.7 | 63.6 | 49.3 | 62.1 | 73.0 | 67.2 |
| EMOLL/SURFACTANT RATIO | 2.74 | 1.98 | 2.04 | 2.30 | 2.71 | 3.10 | a = Polyoxypropylene (6) polyoxyethylene (11) fatty ether, where the chain length of the alcohol is approximately between 12 and 18.
b = Polyethoxylated polypropoxylated short chain ($C_{10}$-$C_{12}$) fatty alcohol sold under the tradename Plurafac C-17 by BASF Wyandotte Corporation of Michigan.
d = Polyoxyethylene (15) lauryl/myristylamine.

Examples 7-12 produced a satisfactory bathing oil that cleansed the skin and deposited a layer of emollient on the skin.

EXAMPLES 13-18

| Components | 13 | 14 | 15 | 16 | 17 | 18 |
|---|---|---|---|---|---|---|
| 1. Primary Emollient | | | | | | |
| isopropyl myristate | 25.0 | 63.7 | 71.2 | 72.2 | 72.2 | 63.6 |
| isopropyl isostearate | 19.0 | | | | | |
| propylene glycol dipelargonate | 9.5 | | | | | |
| isostearyl lactate | | | | | | 0.9 |
| 2. Secondary Emollients | 1.1 | 1.2 | 2.2 | 1.2 | 1.2 | 0.9 |
| 3. Nonionic Surfactant | | | | | | |
| a | 19.0 | 15.0 | 13.3 | 13.3 | 13.3 | 11.7 |
| c | 4.8 | | | | | |
| 4. Cationic Surfactant | | | | | | |
| d | 11.4 | 15.0 | 13.3 | | | |
| e | | | | 13.3 | | 11.7 |
| f | | | | | 13.3 | |
| 5. Perfume | 1.9 | 1.0 | | | | 1.6 |
| 6. Preservative | 0.6 | 0.1 | | | | 0.7 |
| 7. Ethanol | 7.6 | 4.0 | | | | 7.9 |
| 8. 85% lactic acid | | | | | | 0.9 |
| CATIONIC/NONIONIC RATIO | 0.48 | 1.00 | 1.00 | 1.00 | 1.00 | 1.00 |
| TOTAL EMOLLIENT % | 57.4 | 64.9 | 75.4 | 73.2 | 73.2 | 65.4 |
| EMOLL/SURFACTANT RATIO | 1.79 | 2.16 | 2.83 | 2.80 | 2.80 | 2.79 | a = Polyoxypropylene (6) polyoxyethylene (11) fatty ether, where the chain length of the alcohol is approximately between 12 and 18.
c = Polyoxyethylene (2) isostearyl ether.
d = Polyoxyethylene (15) lauryl/myristylamine.
e = Polyoxyethylene (15) palmityl/stearylamine.
f = Polyoxyethylene (5) octadecylamine.

Examples 13-18 produced a satisfactory bathing oil that cleansed the skin and deposited a layer of emollient on the skin.

EXAMPLES 19-24

| Components | 19 | 20 | 21 | 22 | 23 | 24 |
|---|---|---|---|---|---|---|
| 1. Primary Emollient | | | | | | |
| isopropyl myristate | 69.8 | 66.9 | 63.0 | 63.8 | 62.9 | 61.3 |
| isostearyl lactate | 1.0 | 1.0 | 0.9 | 0.9 | | |
| 2. Secondary Emollients | 1.1 | 1.2 | 1.0 | 0.6 | 1.0 | 0.5 |
| 3. Nonionic Surfactant | | | | | | |
| a | 12.8 | 12.3 | 11.6 | 11.8 | | |
| b | | | | | 15.5 | |
| h | | | | | 15.5 | |
| j | | | | | | 1.0 |
| m | | | | | | 14.2 |
| n | | | | | | 15.2 |
| 4. Cationic Surfactant | | | | | | |
| e | 13.8 | 13.3 | 12.5 | 11.8 | 5.2 | 5.1 |
| 5. Perfume | | 3.8 | 1.6 | 1.6 | | 2.0 |
| 6. Preservative | 0.6 | 0.6 | 0.5 | 0.7 | | 0.7 |
| 7. Ethanol | | | 8.1 | 8.0 | | |
| 8. 85% lactic acid | 0.9 | 0.9 | 0.9 | | | |
| 9. Citric acid | | | | 0.7 | | |
| CATIONIC/NONIONIC RATIO | 1.08 | 1.08 | 1.08 | 1.08 | 0.33 | 0.17 |
| TOTAL EMOLLIENT % | 71.8 | 68.1 | 64.9 | 65.3 | 63.9 | 61.8 |
| EMOLL/SURFACTANT RATIO | 2.70 | 2.70 | 2.70 | 2.80 | 1.80 | 2.42 | a = Polyoxypropylene (6) polyoxyethylene (11) fatty ether, where the chain length of the alcohol is approximately between 12 and 18.
b = Polyethoxylated polypropoxylated short chain ($C_{10}$-$C_{12}$) fatty alcohol sold under the tradename Plurafac C-17 by BASF Wyandotte Corporation of Michigan.
e = Polyoxyethylene (15) palmityl/stearylamine.
h = Polyoxyethylene (9) lauryl ether.
j = Block polymer Polyoxyethylene (7) polyoxypropylene 54 polyoxyethylene 7.
m = Tetra (polyoxyethylene (14) polyoxypropylene (12)) ethylenediamine.
n = Polyoxyethylene (8) lauryl ether.

Examples 19-24 produced a satisfactory bathing oil that cleansed the skin and deposited a layer of emollient on the skin.

EXAMPLES 25-30

| Components | 25 | 26 | 27 | 28 | 29 | 30 |
|---|---|---|---|---|---|---|
| 1. Primary Emollient | | | | | | |
| isopropyl myristate | 62.3 | 61.9 | 58.2 | 61.9 | 61.9 | 72.3 |
| 2. Secondary Emollients | 0.5 | 0.5 | 0.5 | 0.5 | 0.5 | 0.6 |
| 3. Nonionic Surfactant | | | | | | |
| j | 1.0 | 1.0 | 1.0 | 1.1 | 1.1 | 2.4 |
| k | | 15.4 | | | | |
| l | | | 19.2 | | | |
| m | 7.2 | | | 7.7 | 12.3 | |
| n | 15.5 | 15.4 | 14.4 | 15.4 | 15.4 | 17.9 |
| o | | | | | 7.7 | 3.1 |
| p | 7.2 | | | | | |
| 4. Cationic Surfactant | | | | | | |
| e | 5.6 | 5.1 | 4.8 | 5.1 | 5.1 | 6.0 |
| 5. Perfume | | | 2.0 | | | |
| 6. Preservative | 0.7 | 0.7 | | 0.6 | 0.6 | 0.8 |
| CATIONIC/NONIONIC RATIO | 0.18 | 0.16 | 0.14 | 0.16 | 0.19 | 0.29 |
| TOTAL EMOLLIENT % | 62.8 | 62.4 | 58.7 | 62.4 | 62.4 | 72.8 |
| EMOLL/SURFACTANT RATIO | | 1.69 | 1.46 | 1.95 | 1.95 | 2.71 | e = Polyoxyethylene (15) palmityl/stearylamine.
h = Polyoxyethylene (9) lauryl ether.
j = Block polymer Polyoxyethylene (7) polyoxypropylene 54 polyoxyethylene 7.
k = Polyoxypropylene (21) polyoxyethylene (7) polyoxypropylene (21).
l = Polyoxyethylene (13) polyoxypropylene (30) polyoxyethylene (13).
m = Tetra (polyoxyethylene (14) polyoxypropylene (12)) ethylenediamine.
n = Polyoxyethylene (8) lauryl ether.
o = Polyoxyethylene sorbitan monostearate.
p = Tetra (polyoxyethylene (19) polyoxypropylene (21)) ethylenediamine Examples 25-30 produced a satisfactory bathing oil that cleansed the skin and deposited a layer of emollient on the skin.

EXAMPLES 31-36

| Components | 31 | 32 | 33 | 34 | 35 | 36 |
|---|---|---|---|---|---|---|
| 1. Primary Emollient | | | | | | |
| isopropyl myristate | 61.9 | 60.7 | 67.0 | 61.6 | 50.8 | 39.8 |

-continued

| Components | 31 | 32 | 33 | 34 | 35 | 36 |
|---|---|---|---|---|---|---|
| sunflower oil | | | | 10.8 | 21.6 | 32.6 |
| 2. Secondary Emollients | 0.5 | 0.5 | 1.1 | 1.2 | 1.2 | 1.2 |
| 3. Nonionic Surfactant | | | | | | |
| a | | 7.0 | 12.2 | 13.2 | 13.2 | 13.2 |
| j | 2.0 | 2.0 | | | | |
| l | 14.3 | 7.0 | | | | |
| n | 15.4 | 15.0 | | | | |
| 4. Cationic Surfactant | | | | | | |
| e | | 5.1 | 5.0 | 12.2 | 13.2 | 13.2 | 13.2 |
| 5. Perfume | | 2.0 | 4.7 | | | |
| 6. Preservative | 0.7 | 0.7 | | | | |
| 7. Ethanol | | | 2.8 | | | |
| CATIONIC/NONIONIC RATIO | 0.16 | 0.21 | 1.00 | 1.00 | 1.00 | 1.00 |
| TOTAL EMOLLIENT % | 62.4 | 61.2 | 68.1 | 73.7 | 73.7 | 73.8 |
| EMOLL/SURFACTANT RATIO | 1.70 | 1.96 | 2.70 | 2.80 | 2.80 | 2.80 | a = Polyoxypropylene (6) polyoxyethylene (11) fatty ether, where the chain length of the alcohol is approximately between 12 and 18.
e = Polyoxyethylene (15) palmityl/stearylamine.
j = Block polymer Polyoxyethylene (7) polyoxypropylene 54 polyoxyethylene 7.
l = Polyoxyethylene (13) polyoxypropylene (30) polyoxyethylene (13).
n = Polyoxyethylene (8) lauryl ether.

Examples 31–36 produced a satisfactory bathing oil that cleansed the skin and deposited a layer of emollient on the skin.

EXAMPLES 37–42

| Components | 37 | 38 | 39 | 40 | 41 | 42 |
|---|---|---|---|---|---|---|
| 1. Primary Emollient | | | | | | |
| isopropyl myristate | 34.3 | 28.0 | 40.0 | 68.7 | 63.7 | 63.7 |
| sunflower oil | 38.0 | 44.5 | | | | |
| soy oil | | | 32.4 | | | |
| 2. Secondary Emollients | 1.2 | 1.2 | 1.2 | 1.2 | 1.2 | 1.2 |
| 3. Nonionic Surfactant | | | | | | |
| a | 13.2 | 13.2 | 13.2 | 12.5 | 12.5 | 12.5 |
| q | | | | | 5.0 | |
| r | | | | | | 5.0 |
| 4. Cationic Surfactant | | | | | | |
| e | 13.2 | 13.2 | 13.2 | 12.5 | 12.5 | 12.5 |
| 5. Perfume | | | | 5.0 | 5.0 | 5.0 |
| CATIONIC/NONIONIC RATIO | 1.00 | 1.00 | 1.00 | 1.00 | 1.00 | 1.00 |
| TOTAL EMOLLIENT % | 74.6 | 73.8 | 73.6 | 70.0 | 65.0 | 65.0 |
| EMOLL/SURFACTANT RATIO | 2.80 | 2.80 | 2.80 | 2.80 | 2.60 | 2.60 | a = Polyoxypropylene (6) polyoxyethylene (11) fatty ether, where the chain length of the alcohol is approximately between 12 and 18.
e = Polyoxyethylene (15) palmityl/stearylamine.
q = Lauric/myristic diethanolamide.
r = Oleyl diethanolamide.

Examples 37–42 produced a satisfactory bathing oil that cleansed the skin and deposited a layer of emollient on the skin.

Although the present invention has been described with reference to preferred embodiments, workers skilled in the art will recognize that changes may be made in form and detail without departing from the spirit and scope of the invention.

What is claimed is:

1. A bathing oil composition comprising:
   a nonionic surfactant selected from the group of ethylene oxide adducts of ethylene diamine, fatty esters and fatty alcohols, block polymers of ethylene oxide and diethanol amine derivatives of fatty acids;
   a cationic surfactant having a relatively high molecular weight greater than approximately 300 and having at least one positively charged nitrogen;
   a primary emollient having hydrophobic characteristics and containing at least one oxygen; and
   wherein the ratio of cationic surfactant to nonionic surfactant is in the approximate range of 0.15 to 1.0 by weight and the cationic and nonionic surfactants combined are at most approximately 50% of the composition by weight.

2. The composition of claim 1 and further including:
   a secondary emollient made from a mixture of lanolin oil or lanolin alcohol, an ethoxylated derivative of lanolin oil, a fatty alcohol selected from the group containing 12 to 18 carbon atoms, a solid fatty acid selected from the group containing 14 to 18 carbon atoms and lecithin.

3. The composition of claim 2 wherein components of the secondary emollient mixture are in approximately equal proportions.

4. The composition of claim 1 wherein the nonionic surfactant is further selected from the group of ethylene oxide and propylene oxide adducts of ethylene diamine, fatty esters and fatty alcohols, and from block polymers of ethylene oxide and propylene oxide and diethanol amine derivatives of fatty acids.

5. The composition of claim 1 wherein the cationic surfactant is selected from the group of salts of polyoxyethylene adducts of primary amines in the range of approximately 12 to 18 carbon atoms, and morpholine based cationic quaternary ammonium compounds which are cationic and surface active.

6. The composition of claim 1 wherein the primary emollient is selected from the group of synthetic esters of a fatty acid or a mixture of a synthetic ester and a natural oily fat such as sunflower or soy oil.

7. The composition of claim 6 wherein the primary emollient is isopropyl myristate.

* * * * *